US006455690B1

(12) United States Patent
Tam et al.

(10) Patent No.: US 6,455,690 B1
(45) Date of Patent: Sep. 24, 2002

(54) L-8-OXO-7-PROPYL-7,8-DIHYDRO-(9H)-GUANOSINE

(76) Inventors: Robert Tam, ICN Pharmaceuticals, Inc., 3300 Hyland Ave., Costa Mesa, CA (US) 92626; Devron Averett, 9050 Camino Santa Fe, San Diego, CA (US) 92121; Guangyi Wang, ICN Pharmaceuticals, Inc., 3300 Hyland Ave., Costa Mesa, CA (US) 92626; Kanda Ramasamy, ICN Pharmaceuticals, Inc., 3300 Hyland Ave., Costa Mesa, CA (US) 92626

( * ) Notice: Subject to any disclaimer, the term of this patent is extended or adjusted under 35 U.S.C. 154(b) by 0 days.

(21) Appl. No.: 09/594,647

(22) Filed: Jun. 15, 2000

Related U.S. Application Data

(60) Division of application No. 09/462,714, filed as application No. PCT/US98/00634 on Jan. 13, 1998, now abandoned, which is a continuation-in-part of application No. PCT/US97/18387, filed on Oct. 15, 1997.
(60) Provisional application No. 60/055,487, filed on Aug. 12, 1997, provisional application No. 60/043,974, filed on Apr. 23, 1997, provisional application No. 60/036,094, filed on Jan. 1, 1997, and provisional application No. 60/028,586, filed on Oct. 16, 1996.

(51) Int. Cl.[7] ............................................. C07H 19/167
(52) U.S. Cl. .................................. 536/27.81; 536/27.13
(58) Field of Search ........................... 536/27.13, 27.81

(56) References Cited

U.S. PATENT DOCUMENTS 4,746,651 A * 5/1988 Goodman .................... 514/45

FOREIGN PATENT DOCUMENTS

| WO | WO98/16184 A2 | * | 4/1998 |
| WO | WO98/30223 A1 | * | 7/1998 |

OTHER PUBLICATIONS

Nagahara et al., "Thiazolo[4,5–d]pyrimidine Nucleosides. The Synthesis of Certain 3–β–D–Ribofuranosylthiazolo[4,5–d]pyrimidines as Potential Immunotherapeutic Agents," *Journal of Medicinal Chemistry*, 33(1), 407–415 (Jan., 1990).*

Smee et al., "Broad Spectrum In Vivo Antiviral Activity of 7–Thia–8–Oxoguanosine, a Novel Immunopotentiating Agent," *Antimicrobial Agents and Chemotherapy*, 33(9), 1487–1492 (Sep., 1989).*

* cited by examiner

Primary Examiner—Gary Geist
Assistant Examiner—L. E. Crane
(74) Attorney, Agent, or Firm—Fish & Associates, LLP; Robert D. Fish

(57) ABSTRACT

Novel nucleosides having the structure of Formula 1 and Formula 2 are contemplated. In one aspect of the invention, controlled release dosage forms are particularly contemplated. Further, alternative routes of administration of the nucleosides having the structure of Formula 1 or Formula 2 are contemplated.

1 Claim, No Drawings

L-8-OXO-7-PROPYL-7,8-DIHYDRO-(9H)-GUANOSINE

This application is a divisional of copending U.S. application Ser. No. 09/462,714, filed on Jul. 9, 1999, now abandoned, which is a 371 of PCT/US98/00634, filed Jan. 13, 1998 and published Jul. 16, 1998 as WO 98/30223, which claims priority based on copendency with U.S. Provisional Application No. 60/055,487, filed on Aug. 12, 1997, now expired, U.S. Provisional Application No. 60/043,974, filed on Apr. 23, 1997, now expired, and U.S. Provisional Application No. 60/036,094, filed on Jan. 1, 1997, now expired.

PCT/US98/00634 is also a continuation-in-part of PCT/US97/18387, filed Oct. 15, 1997 and published on Apr. 23, 1998 as WO 98/16184 which claims priority based on copendency with U.S. Provisional Application No. 60/055,487, filed on Aug. 12, 1997, now expired, U.S. Provisional Application No. 60/043,974, filed on Apr. 23, 1997, now expired, and U.S. Provisional Application No. 60/028,586, filed on Oct. 16, 1996, now expired.

FIELD OF THE INVENTION

The present invention relates to the field of nucleosides.

BACKGROUND OF THE INVENTION

Mammalian immune systems contain two major classes of lymphocytes: B lymphocytes (B cells), which originate in the bone marrow; and T lymphocytes (T cells) which originate in the thymus. B cells are largely responsible for humoral immunity (i.e., antibody production), while T cells are largely responsible for cell-mediated immunity.

T cells are generally considered to fall into two subclasses, helper T cells and cytotoxic T cells. Helper T cells activate other lymphocytes, including B cells and cytotoxic T cells, and macrophages, by releasing soluble protein mediators called cytokines which are involved in cell-mediated immunity. As used herein, lymphokines are a subset of cytokines.

Helper T cells are also generally considered to fall into two subclasses, Th1 and Th2. Th1 cells (also known as Type 1 cells) produce interleukin 2 (IL-2), tumor necrosis factor (TNFα) and interferon gamma (IFNγ), and are responsible primarily for cell-mediated immunity such as delayed type hypersensitivity and antiviral immunity. In contrast, Th2 cells (also known as Type 2 cells) produce interleukins, IL4, IL-5, IL-6, IL-9, IL-10 and IL-13, and are primarily involved in assisting humoral immune responses such as those seen in response to allergens, e.g. IgE and 1gG4 antibody isotype switching (Mosmann, 1989, *Annu Rev Immunol*, 7:145–173).

As used herein, the terms Th1 and Th2 "responses" are meant to include the entire range of effects resulting from induction of Th1 and Th2 lymphocytes, respectively. Among other things, such responses include variation in production of the corresponding cytokines through transcription, translation, secretion and possibly other mechanisms, increased proliferation of the corresponding lymphocytes, and other effects associated with increased production of cytokines, including motility effects.

The mechanisms by which nucleosides and other compounds selectively modulate Th1 and Th2 responses relative to each other are still unclear. One possibility contemplated by the present inventors is that effective nucleosides alter the pool of guanosine triphosphate (GTP), which in turn affects the rate at which cytokines are produced. In this theory, relatively large variations in available GTP are sufficient to affect concentrations of both Th1 and Th2 cytokines, while relatively smaller variations in available GTP tend to affect concentrations of Th1 and Th2 cytokines to different extents.

These discoveries are especially significant because modern treatment strategies for many of the above-listed diseases have either limited effectiveness, significant side effects, or both. Treatment of autoimmune disease, for example, is frequently limited to palliative measures, removal of toxic antibodies (as in myasthenia gravis), and administration of hazardous drugs including corticosteroids, chloroquine derivatives, and antimetabolic or antitumor drugs, and drugs such as cyclosporines which target immune system cells.

SUMMARY OF THE INVENTION

This application relates to novel nucleosides. Nucleosides contemplated are those nucleosides corresponding to Formulas 1 and 2.

DETAILED DESCRIPTION

Where the following terms are used in this specification, they are used as defined below.

The terms "α" and "β" indicate the specific stereochemical configuration of a substituent at an asymmetric carbon atom in a chemical structure as drawn.

The term "aryl" refers to a monovalent unsaturated aromatic carbocyclic radical having a single ring (e.g., phenyl) or two condensed rings (e.g., naphthyl), which can optionally be substituted with hydroxyl, lower alky, chloro, and/or cyano.

The term "enantiomers" refers to a pair of stereoisomers that are non-superimposable mirror images of each other. A mixture of a pair of enantiomers, in a 1:1 ratio, is a "racemic" mixture.

The term "heterocycle" refers to a monovalent saturated or unsaturated carbocyclic radical having at least one hetero atom, such as N, O or S, within the ring each available position of which can be optionally substituted, independently, with, e.g., hydroxy, oxo, amino, imino, lower alkyl, bromo, chloro and/or cyano. Included within this class of substituents are purines, pyrimidines.

The term "isomers" refers to different compounds that have the same formula. "Stereoisomers" are isomers that differ only in the way the atoms are arranged in space.

The term "L-configuration" is used throughout the present invention to describe the chemical configuration of the ribofuranosyl moiety of the compounds that is linked to the nucleobases. The L-configuration of the sugar moiety of compounds of the present invention contrasts with the D-configuration of ribose sugar moieties of the naturally occurring nucleosides such as cytidine, adenosine, thymidine, guanosine and uridine.

The term "lower alky" refers to methyl, ethyl, n-propyl, isopropyl, n-butyl, t-butyl, I-butyl or n-hexyl. This term is further exemplified to a cyclic, branched or straight chain from one to six carbon atoms.

The term "monocyclic" refers to a monovalent saturated carbocyclic radical having at least one hetero atom, such as O N, S, Se or P, within the ring, each available position of which can be optionally substituted, independently, with a sugar moiety or any other groups like bromo, chloro and/or cyano, so that the monocyclic ring system eventually aromatized.

The term "nucleoside" refers to a compound composed of any pentose or modified pentose moiety attached to a specific position of a heterocycle or to the natural position of a purine (9-position) or pyrimidine (1-position).

The term "C-nucleosides" is used throughout the specification to describe the linkage type that formed between the ribose sugar moiety and the heterocyclic base. In C-nucleosides, the linkage originates from the C-1 position of the ribose sugar moiety and joins the carbon of the heterocyclic base. The linkage that forms in C-nucleosides is carbon-to-carbon type.

The term "D-nucleosides" refers to nucleoside compounds that have a D-ribose sugar moiety (e.g., Adenosine).

The term "L-nucleosides" refers to nucleoside compounds that have an L-ribose sugar moiety.

The term "N-nucleosides" is used throughout the specification to describe the linkage type that formed between the ribose sugar moiety and the heterocyclic base. In N-nucleosides, the linkage originates from the C-1 position of the ribose sugar moiety and joins the nitrogen of the heterocyclic base. The linkage that forms in N-nucleosides is carbon to nitrogen type.

The term "nucleotide" refers to a phosphate ester substituted on the 5-position of a nucleoside.

The term "Purine" refers to nitrogenous bicyclic heterocycles depicted in Formula 1 and 2 herein.

Examples of compounds contemplated to be effective in the invention are shown in Formula 1 and 2.

Formula 1 has the structure:

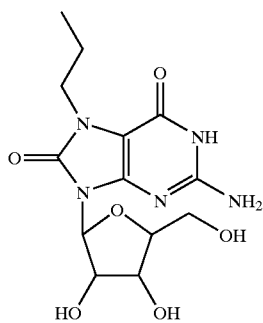

Formula 2 has the structure:

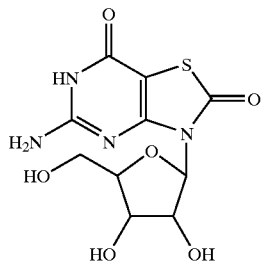

Administration

It is contemplated that compounds according to the present invention will be administered in any appropriate pharmaceutical formulation, and under any appropriate protocol. Preferred monotherapeutic dosages and protocols for such drugs are set forth in the PDR, or are at least available from the manufacturer or distributor.

Of course, one of ordinary skill in the art will recognize that a therapeutically effective amount will vary with the infection or condition to be treated, its severity, the treatment regimen to be employed, the pharmacokinetics of the agent used, as well as the patient (animal or human) treated. Thus, effective dosages may range from 1 mg/kg of body weight, or less, to 25 mg/kg of body weight or more. This dosage range generally produces effective blood level concentrations of active compound ranging from about 0.04 to about 100 micrograms/cc of blood in the patient. It is contemplated, however, that appropriate patient-specific regimens will be developed by administering a small amount, and then increasing the amount until either the side effects become unduly adverse, or the intended effect is achieved.

Administration of compounds according to the present invention may take place orally, parenterally (including subcutaneous injections, intravenous, intramuscularly, by intrastemal injection or infusion techniques), by inhalation spray, or rectally, topically and so forth, and in dosage unit formulations containing conventional non-toxic pharmaceutically acceptable carriers, adjuvants and vehicles.

It is contemplated that compounds according to the present invention can be formulated in admixture with a pharmaceutically acceptable carrier. For example, the compounds of the present invention can be administered orally as pharmacologically acceptable salts. Because the compounds of the present invention are mostly water soluble, they can be administered intravenously in physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the ordinary skill of the art to modify the route of administration and dosage regimen of a particular compound in order to manage the pharmacokinetics of the present compounds for maximum beneficial effect in patients.

In addition, compounds included in combinations according to the present invention may be administered separately or together, and when administered separately this may occur in any order. The amounts of the active ingredient(s) and pharmaceutically active agent(s) and the relative timings of administration will be selected in order to achieve the desired combined therapeutic effect.

Administration routes of compounds according to the present invention may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration.

To prepare therapies according to the present invention, a therapeutically effective amount of a compound is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carrier, such as dextrose, mannitol, lactose and related carriers, diluents, granulating agents, lubricants, binders, disintegrating agents and the like may be used. If desired, the tablets or capsules may be enteric-coated or sustained release by standard techniques.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

It will also be appreciated that in general, the most preferred uses according to the present invention are those in which the active compounds are relatively less cytotoxic to the non-target host cells and relatively more active against the target.

While specific embodiments have been disclosed herein, the scope of the invention is not be limited except through interpretation of the appended claims.

We claim:

1. A nucleoside having the structure of Formula 1:

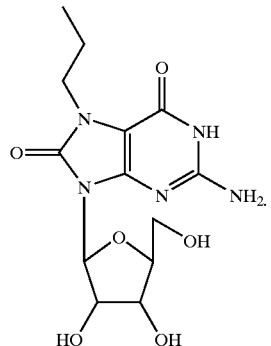

* * * * *